US008672857B2

(12) United States Patent
Muntendam

(10) Patent No.: US 8,672,857 B2
(45) Date of Patent: Mar. 18, 2014

(54) GALECTIN-3 AND CARDIAC RESYNCHRONIZATION THERAPY

(75) Inventor: Pieter Muntendam, Boxford, MA (US)

(73) Assignee: BG Medicine, Inc., Waltham, MA (US)

( * ) Notice: Subject to any disclaimer, the term of this patent is extended or adjusted under 35 U.S.C. 154(b) by 278 days.

(21) Appl. No.: 12/868,612

(22) Filed: Aug. 25, 2010

(65) Prior Publication Data

US 2011/0071583 A1 Mar. 24, 2011

Related U.S. Application Data

(60) Provisional application No. 61/236,712, filed on Aug. 25, 2009.

(51) Int. Cl.
*A61B 5/02* (2006.01)

(52) U.S. Cl.
USPC .......................................................... 600/508

(58) Field of Classification Search
USPC ............ 607/9, 17, 22; 600/508–509; 436/811
See application file for complete search history.

(56) References Cited

U.S. PATENT DOCUMENTS

| | | | |
|---|---|---|---|
| 4,632,901 A | 12/1986 | Valkirs et al. | |
| 4,704,692 A | 11/1987 | Ladner | |
| 4,946,778 A | 8/1990 | Ladner et al. | |
| 5,091,513 A | 2/1992 | Huston et al. | |
| 5,132,405 A | 7/1992 | Huston et al. | |
| 6,319,676 B1 | 11/2001 | Nazareth et al. | |
| 6,485,982 B1 | 11/2002 | Charlton | |
| 6,534,322 B1 | 3/2003 | Sabbadini | |
| 6,889,083 B2 | 5/2005 | Kleckner et al. | |
| 7,041,449 B2 * | 5/2006 | Prolla et al. | 435/6.16 |
| 7,632,234 B2 * | 12/2009 | Manda et al. | 600/508 |
| 7,888,137 B2 | 2/2011 | Pinto | |
| 8,084,276 B2 | 12/2011 | Pinto | |
| 2002/0044932 A1 | 4/2002 | Liu et al. | |
| 2002/0076738 A1 * | 6/2002 | Woo | 435/7.23 |
| 2002/0155513 A1 * | 10/2002 | Hsu et al. | 435/7.23 |
| 2003/0032030 A1 | 2/2003 | Prolla et al. | |
| 2003/0166017 A1 | 9/2003 | McCarthy | |
| 2004/0110221 A1 | 6/2004 | Twine et al. | |
| 2005/0014198 A1 | 1/2005 | Ng | |
| 2005/0084915 A1 | 4/2005 | Woo | |
| 2005/0106100 A1 | 5/2005 | Harris et al. | |
| 2006/0019235 A1 | 1/2006 | Soen et al. | |
| 2006/0019890 A1 | 1/2006 | Kapoun et al. | |
| 2006/0141493 A1 | 6/2006 | West et al. | |
| 2006/0166276 A1 | 7/2006 | Doyle et al. | |
| 2006/0246496 A1 | 11/2006 | Ahmed et al. | |
| 2006/0257946 A1 | 11/2006 | Ding et al. | |
| 2007/0082332 A1 | 4/2007 | Mendrick et al. | |
| 2007/0092886 A1 | 4/2007 | Tabibiazar et al. | |
| 2007/0105105 A1 | 5/2007 | Clelland et al. | |
| 2007/0274959 A1 | 11/2007 | Zeiher et al. | |
| 2008/0193954 A1 * | 8/2008 | Pinto | 435/7.92 |
| 2008/0208167 A1 | 8/2008 | Stankus et al. | |
| 2010/0014954 A1 | 1/2010 | Henderson | |
| 2010/0129927 A1 | 5/2010 | Cleutjens et al. | |
| 2010/0143954 A1 | 6/2010 | Muntendam | |
| 2011/0008805 A1 | 1/2011 | Urdea et al. | |
| 2011/0071583 A1 | 3/2011 | Muntendam | |
| 2011/0104722 A1 | 5/2011 | Pinto | |
| 2011/0137131 A1 | 6/2011 | Adourian et al. | |
| 2012/0029003 A1 | 2/2012 | Muntendam | |
| 2012/0220532 A1 | 8/2012 | Pinto | |
| 2012/0220671 A1 | 8/2012 | Muntendam | |

FOREIGN PATENT DOCUMENTS

| | | |
|---|---|---|
| CN | 1620612 A | 5/2005 |
| JP | 2004-198313 | 7/2004 |
| WO | WO-0157274 | 8/2001 |
| WO | WO-0177389 | 10/2001 |
| WO | WO-03031650 | 4/2003 |
| WO | WO-03071279 | 8/2003 |
| WO | WO-2004038376 | 5/2004 |
| WO | WO-2004048933 | 6/2004 |
| WO | WO-2004063334 | 7/2004 |
| WO | WO-2004111654 | 12/2004 |
| WO | WO-2005023314 | 3/2005 |
| WO | WO-2005040817 A1 | 5/2005 |
| WO | WO-2005070446 | 8/2005 |
| WO | WO-2006026074 | 3/2006 |
| WO | WO-2006083986 | 8/2006 |
| WO | WO-2010096126 A1 | 8/2010 |
| WO | WO-2011031493 A2 | 3/2011 |
| WO | WO-2012003475 A1 | 1/2012 |
| WO | WO-2012106341 A1 | 8/2012 |
| WO | WO-2012162531 A1 | 11/2012 |
| WO | WO-2013103984 A2 | 7/2013 |

OTHER PUBLICATIONS

Beshai et al. (2007) "Cardiac-Resynchronization Therapy in Heart Failure with Narrow QRS Complexes," *N. Engl. J. Med.* 357:2461-2471.

Clackson et al. (1991) "Making antibody fragments using phage display libraries," *Nature* 352:624-628.

Cleland et al. (2005) "The Effect of Cardiac Resynchronization on Morbidity and Mortality in Heart Failure," *New Engl. J. Med.* 352:1539-49.

Duray et al. (2008) "Upgrading to biventricular pacing/defibrillation systems in right ventricular paced congestive heart failure patients: prospective assessment of procedural parameters and response rate," *Europace* 10:48-52.

(Continued)

*Primary Examiner* — Rex R Holmes
(74) *Attorney, Agent, or Firm* — Goodwin Procter LLP

(57) ABSTRACT

The present invention relates to materials and methods for monitoring and predicting a heart failure patient's physiological response to cardiac resynchronization therapy. More specifically, the present invention relates to the endogenous protein galectin-3 and its use in monitoring progression of disease in a patient undergoing cardiac resynchronization therapy, and as a predictor of response to cardiac resynchronization therapy.

55 Claims, No Drawings

(56) References Cited

OTHER PUBLICATIONS

Fruhwald et al. (2007) "Early and sustained effects of cardiac resynchronization therapy on N-terminal pro-B-type natriuretic peptide in patients with moderate to severe heart failure and cardiac dyssynchrony," *Eur. Heart J.* 28:1592-1597.
Gabius (2006) "Cell Surface Glycans: The Why and How of Their Functionality as Biochemical Signals in Lectin-Mediated Information Transfer," *Crit. Rev. Immunol.* 26:43-79.
Hagberg (1998) "From magnetic resonance spectroscopy to classification of tumors. A review of pattern recognition methods," *NMR Biomed.* 11:148-156.
Hawkins et al. (2006) "Selecting patients for cardiac resynchronization therapy: electrical or mechanical dyssynchrony?," *Eur. Heart J.* 27:1270-1281.
Henderson et al. (2006) "Galectin-3 regulates myofibroblast activation and hepatic fibrosis," *Proc. Natl. Acad. Sci. USA* 103:5060-5065.
Jeevantham et al. (2009) "Cardiac resynchronization therapy in heart failure patients: An update," *Cardiol J.* 16(3):197-209.
Kuwabara et al. (1996) "Galectin-3 Promotes Adhesion of Human Neutrophils to Laminin," *J. Immunol.* 156(10):3939-3944.
Leclercq et al. (2002) "Retiming the Failing Heart: Principles and Current Clinical Status of Cardiac Resynchronization," *J. American Coll. Of Card.* 39:194-201.
Liu et al. (2009) "N-acetyl-seryl-aspartyl-lysyl-proline prevents cardiac remodeling and dysfunction induced by galectin-3, a mammalian adhesion/growth-regulatory lectin," *Am. J. Physiol. Heart Circ. Physiol.* 296:H404-H412.
Lok et al. (2007) *Eur. Heart J.* 28:141, Abstract 1035.
Papaspyridonos et al. (2008) "Galectin-3 Is an Amplifier of Inflammation in Atherosclerotic Plaque Progression Through Macrophage Activation and Monocyte Chemoattraction," *Arterioscler. Thromb. Vasc. Biol.* 28(3):433-440.
Rovner et al. (2007) "Relation of Left Ventricular Lead Placement in Cardiac Resynchronization Therapy to Left Ventricular Reverse Remodeling and to Diastolic Dyssynchrony," *Am. J. Cardiol.* 99:239-241.
Sano et al. (2000) "Human Galectin-3 Is a Novel Chemoattractant for Monocytes and Macrophages," *J. Immunol.* 165(4):2156-2164.
Sharma et al. (2004) "Galectin-3 Marks Activated Macrophages in Failure-Prone Hypertrophied Hearts and Contributes to Cardiac Dysfunction," *Circulation* 110:3121-3128.
Stellbrink (2007) "It's the metabolism, stupid! Why electrophysiologists should be interested in biomarkers of heart failure," *Eur. Heart J.* 28:1541-1542.
van Kimmenade et al. (2006) "Utility of Amino-Terminal Pro-Brain Natriuretic Peptide, Galectin-3, and Apelin for the Evaluation of Patients With Acute Heart Failure," *J. Am. Coll. Cardiol.* 48:1217-1224.
Ahmed et al. (2007) "Advanced Glycation Endproducts: What is their relevance to diabetic complications?" *Diabetes, Obesity and Metab.* 9(3):233-245.
Almkvist et al. (2004) "Galectins as inflammatory mediators," *Glyconconj. J.* 19:575-581.
Andre et al. (2001) "Wedgelike Glycodendrimers as Inhibitors of Binding of Mammalian Galectins to Glycoproteins, Lactose Maxiclusters, and Cell Surface Glycoconjugates," *CHEMBIOCHEM* 2:822-830.
Aragno et al. (2005) "Up-regulation of advanced glycated products receptors in the brain of diabetic rats is prevented by antioxidant treatment," *Endocrinology* 146(12):5561-5567.
Aragno et al. (2006) "Oxidative Stress-Dependent Impairment of Cardiac-Specific Transcription Factors in Experimental Diabetes," *Endocrinology* 147(12):5967-5974.
Bandman et al. (2002) "Complexity of Inflammatory Responses in Endothelial Cells and Vascular Smooth Muscle Cells Determined by Microarray Analysis," *Ann. NY. Acad. Sci.* 975:77-90.
Barboni et al. (2000) "Molecular modeling and mutagenesis studies of the N-terminal domains of galectin-3: evidence for participation with the C-terminal carbohydrate recognition domain in oligosaccharide binding," *Glycobiology* 10:1201-1208.
Barondes et al. (1994) "Galectins: A family of Animal β-Galactoside-Binding Lectins," *Cell* 76:597-598.
Bender MedSystems product information and manual for enzyme-linked immunosorbent assay for quantitative detection of human Galectin-3, BMS279/2, dated Aug. 24, 2006, 32 pages.
BGM Galectin-3 assay; Product Insert (US); BG Medicine, Inc., Mar. 2011.
Bohlender et al. (2005) "Advanced glycation end products and the kidney," *Am. J. Physiol.: Renal Physiol.* 289:F645-F659.
Bolli (2002) "Clinical strategies for controlling peaks and valleys: type 1 diabetes," *IJCP* 10 pages.
Boluyt et al. (1995) "The ageing spontaneously hypertensive rat as a model of the transition from stable compensated hypertrophy to heart failure," *Eur. Heart J.* 19-30.
Boluyt et al. (1995) "The lonely failing heart: a case for ECM genes," *Cardio. Res.* 836-340.
Boluyt et al. (2000) "Matrix gene expression and decompensated heart failure: The aged SHR model," *Cardio. Res.* 239-249.
Braunwald (2008) "Biomarkers in heart failure," *N. Engl. J. Med.* 20:2148-59.
Broers et al. (1999) "Dynamics of the nuclear lamina as monitored by GFP-tagged A-type lamins," *J. Cell Sci.* 112:3463-3475.
Brooks et al. (1997) "Captopril Modifies Gene Expression in Hypertrophied and Failing Hearts of Aged Spontaneously Hypertensive Rats," *Hypertension* 1362-1368.
Cameselle-Teijeiro et al. (2005) "Cystic tumor of the atrioventricular node of the heart appears to be the heart equivalent of the solid cell nests (ultimobranchial rests) of the thyroid," *Am. J. Clin. Pathol.* 123(3):369-375.
Cheng et al. (2007) "Differential neuroprotective effects of a minocycline-based drug cocktail in transient and permanent focal cerebral ischemia," *Exp. Neurol.* 204(1):433-442.
Cherayil et al. (1990) "Molecular cloning of a human macrophage lectin specific for galactose," *Proc. Natl. Acad. Sci. USA* 7324-7328.
Christenson et al. (2010) "Multi-center determination of galectin-3 assay performance characteristics: anatomy of a novel assay for use in heart failure," *Clin. Biochem.* 43:683-90.
Cleutjens et al. (1995) "Collagen Remodeling after Myocardial Infarction in the Rat Heart," *Am. J. Pathol.* 147:325-338.
Cleutjens et al. (1999) "Thrombospondin 2 Deficiency in Mice Results in Cardiac Rupture Early after Myocardial Infarction," *Circulation* (abstract).
Cohn et al. (2000) "Cardiac remodeling—concepts and clinical implications: a consensus paper from an international forum on cardiac remodeling," *J. Am. Coll. of Cardiol.* 35:569-82.
Cooper (2002) "Galectinomics: Finding themes in complexity," *Biochim. Biophys. Acta.* 1572:209-231.
Cosson (2004) "Usefulness of B-type Natriuretic Pepetide (BNP) as a screen for left ventricular abnormalities in diabetes mellitus," *Diabetes Metab.* 30:381-6.
Czekalski (2007) "BNP concentrations in diabetics with dyspnea," printed on Sep. 14, 2007, 4 pages.
de Boer et al. (2009) "Galectin-3: a novel mediator of heart failure development and progression," *Eur. Heart J.* 11:811-817.
de Boer et al. (2010) "Clinical and prognostic value of galectin-3: a novel fibrosis-associated biomarker. Relation with clinical and biochemical correlates of heart failure," *J. Am. Coll. of Cardiol.* 55(10A):A26.E243. (Presented at the American College of Cardiology Annual Scientific Session, 2010, Atlanta, GA).
de Boer et al. (2010) "Galectin-3 in cardiac remodeling and heart failure," *Curr. Heart Fail. Rep.* 7:1-8.
de Boer et al. (2011) "Predictive Value of Plasma Galectin-3 levels in Heart Failure with Reduced and Preserved Ejection Fraction," *Ann. Med.* 43(1):60-8.
de Couto et al. (2010) "Early Detection of Myocardial Dysfunction and Heart Failure," *Nat. Rev. Cardiol.* 7(6):334-44.
deFilippi et al. (2009) "Clinical validation of a novel assay for galectin-3 for risk assessment in acutely destabilized heart failure," *J. Card. Fail.* 5:S9. (Presented at the Heart Failure Society of America Annual Scientific Meeting, 2009, Boston, MA).

(56) References Cited

OTHER PUBLICATIONS deFilippi et al. (2010) "Galectin-3 in heart failure-linking fibrosis, remodeling, and progression," *US Cardiology*. 7:67-70.

Dumic et al. (2006) "Galectin-3: an open-ended story." *Biochim. Biophys. Acta*. 1760:616-35.

Epshteyn (2003) "Utility of B-Type Natriuretic Peptide (BNP) as a Screen for Left Ventricular Dysfuntion in Patients With Diabetes," *Diabetes Care*. 26(7):2081-2087.

Felker et al. (2010) "Prognostic value of Galectin-3 in chronic heart failure: results from the HF-ACTION study." (Presented at the European Society of Cardiology Congress, 2010, Stockholm, Sweden) p. 429.

Gabius (1990) "Influence of Type of Linkage and Spacer on the Interaction of beta-Galactoside-Binding Proteins with Immobilized Affinity Ligands," *Anal. Biochem*. 91-94.

Giordanengo et al. (2001) "Anti-galectin-1 autoantibodies in human Trypansosoma cruzi infection: differential expression of this β-galactosie-binding protein in cardiac Chagas' disease," *Clin. Exp. Immunol*. 124:266-273.

Grandin et al. (2011) "Galectin-3 and the development of heart failure after acute coronary syndrome: A pilot experience from PROVE IT-TIMI 22," *J. Am. Coll. of Cardiol*. 57:69.

Hein et al. (2003) "Progression From Compensated Hypertrophy to Failure in the Pressure-Overloaded Human Heart: Structural Deterioration and Compensatory Mechanism," *J. Am. Heart Assoc*. 984-991.

Henderson et al. (2008) Galectin-3 expression and secretion links macrophages to the promotion of renal fibrosis, *Am. J. Pathol*. 172:288-98.

Henderson (2009) "The regulation of inflammation by galectin-3," *Immunol. Rev*. 230:160-71.

Hsu et al. (1999) "Galectin-3 expression is induced in cirrhotic liver and hepatocellular carcinoma," *Int. J. Cancer*. 81:519-26.

International Preliminary Report, for International Application No. PCT/EP2004/10879, mailed Sep. 20, 2005.

International Search Report and Written Opinion for International Application No. PCT/EP2004/10879, mailed Nov. 25, 2004, 14 pages.

International Search Report and Written Opinion for International Application No. PCT/US2010/046689 dated May 18, 2011, 10 pages.

Iurisci et al. (2000) "Concentrations of Galectin-3 in the Sera of Normal Controls and Cancer Patients," *Clin. Cancer Res*. 6:1389-1393.

Kankova et al. (2005) "Haplotype Analysis of the RAGE gene: Identification of a Haplotype Marker for Diabetic Nephropathy in Type 2 Diabetes Mellitus," *Nephrol. Dialysis Transport*. 20(6):1093-1102.

Karlsen et al. (2006) "Immune-mediated beta-cell destruction in vitro and in vivo—A pivotal role for galectin-3," *Biochem. Biophys. Res. Commun*. 344(1):406-415.

Kasper et al (1996) "Immunocytochemical evidence for a modulation of galectin-3 (Mac2), a carbohydrate binding protein, in pulmonary fibrosis," *J. Pathol*. 179:309-316.

Kim et al. (2007) "Expression and immunohistochemical localization of galectin-3 in various mouse tissues," *Cell Biol. Int*. 31:655-62.

Kolatsi-Joannou et al. (2011) "Modified citrus pectin reduces galectin-3 expression and disease severity in experimental acute kidney injury," *PLoS One*. 6(4):e18683.

Kostin et al. (2003) "Mycocytes Die by Multiple Mechanisms in Failing Human Hearts," *Cir. Res*. 1-11.

Lainscak et al. (2010) "Clinical trials update from the Heart Failure Society of America Meeting 2009: FAST, IMPROVE-HF, COACH galectin-3 substudy, HF-ACTION nuclear substudy, DAD-HF, and MARVEL-1," *Eur. J. Heart Fail*. 12(2):193-6.

Lambert et al. (2008) "Macrophage roles following myocardial infarction," *Int. J. Cardiol*. 130:147-58.

Liehn et al. (2005) "CCR5-but not CCR1-deficiency protects against neointima formation in apolipoprotein E-deficient mice," *Eur. Heart J*. 26(Suppl 1):239.

Lin et al. (2009) "The relationship between serum galectin-3 and serum markers of cardiac extracellular matrix turnover in heart failure patients," *Clin. Chim. Acta*. 409:96-9.

Liu et al. (2009) "Angiotensin-converting Enzyme is a Modifier of Hypertensive End Organ Damage," *J. Biol. Chem*. 284(23):15564-15572.

Liu et al. (1995) "Expression and function of galectin-3, a beta-galactoside-binding lectin, in human monocytes and macrophages," *American Journal of Pathology*. 147(4):1016-1028.

Lok et al. (2007) "Galectin-3, a novel marker of macrophage activity, predicts outcome in patients with stable chronic heart failure," *J. Am. Coll. of Cardiol*. 49(9) Suppl. A: 98A.

Lok et al. (2010) "Plasma galectin-3 levels predict left ventricular remodeling determined by sequential echocardiography: results from the Deventer-Alkmaar heart failure study," *J. Am. Coll. of Cardiol*. 55(10A):A17. (Presented at the American College of Cardiology Annual Scientific Session, 2010, Atlanta, GA).

Lok et al. (2010) "Prognostic value of galectin-3, a novel marker of fibrosis, in patients with chronic heart failure: data from the DEAL-HF study," *Clin. Res. Cardiol*. 99:323-8.

Lorell et al. (2000) "Left Ventricular Hypertrophy: Pathogenesis, Detection, and Prognosis," *Circulation* 470-479.

Luft et al. (1999) "Hypertension-Induced End-Organ Damage: A New Transgenic Approach to an Old Problem," *Hypertension*. 33:212-218.

Lukyanov et al. (2005) "Galectin-3 interacts with membrane lipids and penetrates the lipid bilayer," *Biochem. Biophys. Res. Commun*. 338:1031-6.

Mathews et al. (1995) "Evidence for IgG Autoantibodies to Galectin-3, a β-Galactoside-Binding Lectin (Mac-2, ε Binding Protein, or carbohydrate Binding Protein 35) in Human Serum," *J. Clin. Immunol*. 15(6):329-337.

McCowan et al. (2009) "Hypertensive Emergencies," *Emedicine*. 1-23.

Menon et al. (1999) "Determinants in the N-terminal domains of galectin-3 for secretion by a novel pathway circumventing the endoplasmic reticulum-Golgi complex." *Eur. J. Biochem*. 264:569-76.

Mensah-Brown et al. (2006) "Functional Capacity of Macrophages Determines the Induction of Type 1 Diabetes," *Annals NY Acad. of Sci*. 1084:49-57.

Milting et al. (2008) "Plasma biomarkers of myocardial fibrosis and remodeling in terminal heart failure patients supported by mechanical circulatory support devices," *J. Heart Lung Transplant*. 27(6):589-96.

Mita et al. (2007) "Swings in blood glucose levels accelerate atherogenesis in apolipoprotein E-deficient mice," *Biochem. Biophys. Res. Commun*. 358(3):679-685.

Moore et al. (2005) "Using Peripheral Blood Mononuclear Cells to Determine a Gene Expression Profile of Acute Ischemic Stroke: A Pilot Investigation," *Circulation*. 111(2):212-221.

Muntendam et al. (2009) "Reference interval for plasma galectin-3 in healthy subjects age 55 years and older," *Clin. Chem.*, 55(6):B72. (Presented at the American Association for Clinical Chemistry Annual Meeting, 2009, Chicago, IL).

Nesto et al. (2003) "Thiazolidinedione use, fluid retention, and congestive heart failure: a consensus statement from the American Heart Association and American Diabetes Association," *Circulation*. 108(23):2941-2948.

Nesto (2007) "CHF in Diabetes: Implications for the Use of TZDs (Slides with Transcript)," http://cme.medscape.com/viewarticle560872_print, 17 pages.

Nishi et al. (2007) "Role of galectin-3 in human pulmonary fibrosis," *Allergol. Int*. 56:57-65.

Ochieng et al. (2004) "Extracellular functions of galectin-3," *Glycoconj. J*. 19:527-535.

Ogawa et al. (2003) "Plasma BNP Levels in the Treatment of Type 2 Diabetes with Pioglitazone," *J. Clin. Endocrinol. Metabol*. 88(8):3993-3996.

Opie et al. (2006) "Controversies in ventricular remodelling," *Lancet*. 367:356-67.

"Panel Discussion (Slides with Transcript)," published Aug. 8, 2007, http://cme.medscape.com/viewarticle/560873, 6 pages.

(56) References Cited

OTHER PUBLICATIONS

Panidis (1984) "Development and Regression of Left Ventricular Hypertrophy," *J. Am. Coll. of Cardiol.* 3(5):1309-20.

Papaspyridonos et al. (2006) "A Potential Role for Galectin-3 in Atherosclerotic Plaque Progression through Monocyte Chemoattraction and Macrophage Activation" *Atherosclerosis.* 186(2):S3.

Pieters (2006) "Inhibition and Detection of Galectins," *ChemBioChem* 7:721-728.

Plutzky (2007) "What Do We Know About Surrogate Markers and Disease Outcomes? (Slides with Transcript)," http://cme.medscape.com/viewarticle/560871_print, 13 pages.

Pokharel et al. (2002) "N-Acetyl-Ser-Asp-Lys-Pro Inhibits Phosphorylation of Smad2 in Cardiac Fibroblasts," *Hypertension.* 155-161.

Psarras et al. (2011) "Regulation of adverse remodelling by osteopontin in a genetic heart failure model," *Eur. Heart J.* epub Jul. 20, 2011, 1-10.

Pugliese et al. (2006) "Increased Glomerular Cell (Podocyte) Apoptosis in Rats with Streptozotocin-induced Diabetes Mellitus: Relation to Increased p53 Expression," *Diabetologia.* 49(Suppl 1):651-652.

Rabinovich et al. (2002) "Role of galectins in inflammatory and immunomodulatory processes." *Biochimica et Biophysica Acta.* 1572:274-284.

Reifenberg et al. (2007) "Interferon-gamma Induces Chronic Active Myocarditis and Cardiomyopathy in Transgenic Mice," *Am. J. of Pathol.* 171(2):463-472.

Rossignol et al. (2010) Galectin-3 and PIIINP are associated with cardiovascular outcomes in patients with heart failure, left ventricular dysfunction and dyschrony. Insights from the CARE-HF study. (Presented at the European Society of Cardiology Congress, 2010, Stockholm, Sweden) 429.

Sano et al. (2003) "Critical role of galectin-3 in phagocytosis by macrophages," *J. Clin. Invest.* 112:389-397.

Sasaki et al. (1999) "Galectin-3 modulates rat mesangial cell proliferation and matrix synthesis during experimental glomerulonephritis induced by anti-Thy1.1 antibodies," *J. Pathol.* 187:481-9.

Sathisha et al. (2007) "Inhibition of galectin-3 mediated cellular interactions by pectic polysaccharides from dietary sources," *Glycoconj. J.* 24:497-507.

Sato et al. (2008) Galectins as danger signals in host-pathogen and host-tumor interactions: new members of the growing group of "alarmins"? Galectins John Wiley & Sons; Eds: Klyosov AA, Zbigniew JW, Platt D. 2008;DOI:IO.1002/9780470378076.ch7. 115-145.

Schroen et al. (2003) "Genomic analysis identifies Thrombospondin-2 as a molecular predictor of heart failure," *Circulation.* 108(17 Suppl.):IV-260.

Schroen et al. (2007) "Lysosomal Integral Membrane Protein 2 is a Novel Component of the Cardiac Intercalated Disc and Vital for Load-induced Cardiac Myocyte Hypertrophy," *J. Exp. Medicine.* 204(5):1227-1235.

Scott-Burden et al. (1998) "Modulation of Extracellualr Matrix by Angiotensin II: Stimulated Glycoconjugate Synthesis and Growth in Vascular Smooth Muscle Cells," *J. Cardio. Pharmacol.* 16(Suppl. 4):S36-S41.

Seetharaman et al. (1998) "X-ray crystal structure of the human galectin-3 carbohydrate recognition domain at 21-A resolution," *J. Biol. Chem.* 273(21):13047-13052.

Shah et al. (2010) "Galectin-3, cardiac structure and function, and long-term mortality in patients with acutely decompensated heart failure," *Eur. J. Heart Fail.* DOI:10.1093/eurjhf/hfq091, 12:826-832.

Shah et al. (2010) "Galectin-3, cardiac structure and function, and long-term mortality in patients with acute heart failure," *J. Am. Coll. of Cardiol.* 55(10A):A34.E329. (Presented at the American College of Cardiology Annual Scientific Session, 2010, Atlanta, GA).

Sharma et al. (2003) "Galectin-3 is a novel macrophage derived mediator of cardiac fibrosis and specifically marks failing hearts," *Circulation.* 108(17 Suppl.):IV-261.

Sharma et al. (2005) "Early growth regulator-1 mediates galectin-3 induced cardiac fibrosis," *Hypertension.* 46:819-820.

Sharma et al. (2005) "Mice lacking galectin-3 exhibit preserved cardiac function and decreased fibrosis following angiotensin II infusion," *Circulation.* 112(17) Suppl S:II-64-II-65.

Sharma et al. (2006) "Novel Anti-inflammatory Mechanisms of Ac-SDKP in High Blood Pressure-induced Target Organ Damage," *Circulation.* 114(18) Suppl II S:240.

Sharma et al. (2008) "Novel anti-inflammatory mechanisms of N-acetyl-ser-asp-lys-pro in hypertension-induced target organ damage," *Am. J. Physiol. Heart Circ. Physiol.* 294:HI226-32.

Sherwi et al. (2010) "Does the severity of LV dysfunction or the extent of myocardial scar explain elevations in plasma galectin-3 in patients with heart failure," *Eur. J. Heart Fail. Suppl.* 9:S18.

Shirakata et al. (2001) Inverse regulation of the angiogenesis factor VEGF and the angiogenesis inhibitors Thrombospondin-1 and TSP-2 in human epidermal keratinocytes, *J. Invest. Dermatol.* 117(2):391.

Smith et al. (2009) "Analytical performance of an optimized ELISA for galectin-3," *Clin. Chem.* 55(6):B69.

Son (2007) "Cardiomyocyte expression of PPARγ leads to cardiac dysfuntion in mice," *J. Clin. Invest.* http://www.jci.org. 1-11.

Stitt et al. (2005) "Impaired Retinal Angiogenesis in Diabetes: Role of Advanced Glycation End Products and Galectin-3," *Diabetes.* 53:785-794.

Tan et al. (2002) "The gene expression fingerprint of human heart failure," *PNAS* 19(17):11387-11392.

Tan et al. (2007) "AGE, RAGE and ROS in Diabetic Neuropathy," *Seminars in Nephrol.* 27(2):130-143.

Tang et al. (2007) "National Academy of Clinical Biochemistry Laboratory Medicine Practice Guidelines; Clinical Utilization of Cardiac Biomarker Testing in Heart Failure," *Circulation* 116(5):e99-e109.

Tang et al. (2011) "Usefulness of Plasma Galectin-3 Levels in Systolic Heart Failure to Predict Renal Insufficiency and Survival," *Am. J. Cardiol.* 108(3):385-90.

Topol et al. (2001) "Single Nucleotide Polymorphisms in Multiple Novel Thrombospondin Genes May Be Associated With Familial Premature Myocardial Infarction," *Circulation* 104:2641-2644.

Ueland et al. (2011) "Galectin-3 in heart failure: high levels are associated with all-cause mortality," *Int. J. Cardiol.* 150(3):361-4.

van Kimmenade et al. (2005) "Galectin-3 predicts 60 days mortality in heart failure: A step towards multimarker strategy in heart failure. Results from the ProBNP investigation of dyspnea in the emergency department (PRIDE) study," *Circulation* 112(17) Suppl S:II-669.

van Veldhuisen et al. (2009) "Clinical and prognostic value of galectin-3, a novel fibrosis-associated biomarker, in patients with chronic heart failure," *J. Card. Fail.* 15(9):814.

Vasan et al. (2003) "Inflammatory Markers and Risk of Heart Failure in Elderly Subjects Without Prior Myocardial Infarction: The Framingham Heart Study," *Circulation* 1486-1491.

Wada et al. (2001) "Galectins, Galactoside-Binding Mammalian Lectins: Clinical Application of Multi-Functional Proteins," *Acta. Med. Okayama* 55(1):11-17.

Walton et al. (2003) "Thrombospondin-2 and lymphotoxin-alpha gene variations predict coronary heart disease in a large prospective study," *Circulation* 108(17 Suppl.):IV-771.

Wu et al. (2004) "The Effect of Diabetes on B-Type Natriuretic Peptide Concentrations in Patients With Acute Dyspnea," *Diabetes Care* 27(10):2398-2404.

Yanavitski et al. (2011) "Novel Biomarkers in Acute Heart Failure," *Curr. Heart Fail. Rep.* 8(3):206-11.

Yang et al. (2008) "Galectins: Structure, function and therapeutic potential," *Expert Rev. Mol. Med.* 10(el7):1-24.

Zhang et al. (2003) "The role of the Grb2-p38 MAPK signaling pathway in cardiac hypertrophy and fibrosis," *J. Clin. Invest.* 111:833-841.

Zile et al. (2010) "Plasma galectin-3 levels in patients with structural and clinical manifestations of hypertensive heart disease: relationship to determinants of matrix composition." (Presented at the American Heart Association Scientific Sessions, 2010, Chicago, IL) *Circulation.* 122.

(56) References Cited

OTHER PUBLICATIONS

"BG Medicine Research Innovation Award," BG Medicine, <http://www.galectin-3.com/researchgrant/>.

bioMerieux: Cardiovascular Diseases: Prognosis in heart failure, Web: http://www.biomerieux-diagnostics.com/servlet/srt/bio/clincial-diagnostics/dynPage?open=CNL__HCP__CRD__PHF&doc=CNL__HCP__CRD__PHF__G__CHP__TXT__1&pubparams.sform=1&lang=en. pp. 1-2, Sep. 6, 2012.

Brott et al. (2011) "2011 ASA/ACCF/AHA/AANN/AANS/ACR/ASNR/CNS/SAIP/SCAI/SIR/SNIS/SVM/SVS Guideline on the management of patients with extracranial carotid and vertebral artery disease: executive summary," *J Am Coll Cardiol*. 57(8):1002-44.

Demetter et al. (2008) "The Galectin Family and Digestive Disease," *J. Pathol*. 215:1-12.

Erkilet et al. (2010) "181: Plasma galectin 3 is increased in terminal heart failure patients and is elevated in patients not surviving mechanical circulatory support," *J. of Heart and Lung Transplantation*. 29(2):S65.

Francia et al. (2007) "Cardiac resynchronization therapy increases plasma levels of the endogenous inotrope apelin.," *Eur. J. Heart Fail*. 9(3):306-309.

"Galectin-3," BG Medicine, <http://www.galectin-3.com/home/about/galectin-3-inhibition/>, printed Nov. 7, 2012.

"Galectin-3," Laboratory Corporation of America, <https://www.labcorp.com/wps/portal/!ut/p/c1/04__SB8K8xLLM9MSSzPy8xBz9CP0os__hACzOQCM__IwMLXyM3AyNjMycDU2dXQwN3M6B8JG55AwMCuv088nNT9Qtyl8oBPK__DWA!!/dl2/d1/L0IDU0NTQ1FvS1VRIS9JSFJBQUInb0FNeUtibTZtL1ICSkp3NDU0a3N1eWx3ISEvN19VRTRTMUk5MzBPR1MyMEITM080TjJONjY4MC9zZWFyY2hCeUtleXdvcmQ!/?criterion=004110>, printed May 20, 2011.

Ho et al. (2012) "Galectin-3, a marker of cardiac fibrosis, predicts incident heart failure in the community," *J. American College of Cardiology*. (60)14:1249-56.

Inohara et al. (2008) "Cytoplasmic and serum galectin-3 in diagnosis of thyroid malignancies," *Biochemical and Biophysical Research Communications*. 376:605-610.

International Search Report and Written Opinion for International Application No. PCT/US2011/042846 dated Oct. 20, 2011, 11 pages.

Levitan et al. (2009) "Consistency with the DASH diet and incidence of heart failure," *Arch Intern Med*. 169(9):851-857.

Liu et al. (1996) "Modulation of functional properties of galectin-3 by monoclonal antibodies binding to the non-lectin domains," *Biochemistry*. 35:6073-6079.

Lok et al. (2007) "Relationship between galectin-3 and NT pro-BNP and outcome in patients with chronic congestive heart failure," *Eur. Heart J*. 28:141, Abstract 1035, http:/cic.escardio.org/abstractdetails.aspx?id-50976&eevtid-19, 1 page.

Mayo Clinic, Test ID: Gal3, Galectin-3, Serum. Web: http://mayomedicallaboratories.com/test-catalog/clinical+and+interpretive/86202. p. 1-2, Sep. 6, 2012.

Nachtigal et al. (1998) "Galectin-3 expression in human atherosclerotic lesions," *Am J. of Pathology*. 152(5):1199-1208.

Ohshima et al. (2003) "Galectin 3 and its binding protein in rhematoid arthritis," *Arthritis & Rheumatism*. 48(10):2788-2795.

Rocchiccioli et al. (2010) "Biomarkers in heart failure: a clinical review," *Heart Fail Rev*. 15:251-273.

Saggiorato et al. (2001) "Galectin-3 as a presurgical immunocytodiagnostic marker of minimally invasive follicular thyroid carcinoma," *J. Clin. Endo. & Met*. 86(11):5152-5158.

Supplementary European Search Report for EP 10815852.8 mailed Jul. 16, 2013, 6 pages.

Zhu and Ochieng (2001) "Rapid Release of Intracellular Galectin-3 from Breast Carcinoma Cells by Fetuin," *Cancer Research*. 61:1869-1873.

\* cited by examiner

GALECTIN-3 AND CARDIAC RESYNCHRONIZATION THERAPY

REFERENCE TO RELATED APPLICATION

This application claims the benefit of U.S. Provisional Application No. 61/236,712, filed Aug. 25, 2009, the complete contents of which are incorporated by reference herein.

BACKGROUND

Congestive heart failure, or heart failure, is a major cause of morbidity and mortality. Approximately 5 million people in the United States suffer from heart failure, with approximately 500,000 new cases diagnosed annually. In many cases, congestive heart failure patients also suffer an arrhythmia further reducing the heart's efficiency.

One treatment option for such patients involves implantation of a cardiac resynchronization therapy (CRT) device, also known as a biventricular pacing device. In a normal heartbeat, the two atrial chambers of the heart contract in unison, pumping blood into the two ventricular chambers. Less than a second later, the two ventricular chambers contract in unison, pumping the blood out of the heart and throughout the body. Some heart failure patients have an electrical delay between the ventricles, such that the two ventricular chambers no longer contract at the same time. The result is a substantial reduction in cardiac output. For example, in a normal heartbeat more than half of the blood in the left ventricle is pumped out with each heart beat. In other words, the "left ventricular ejection fraction" or "LVEF" is greater than 50%. In contrast, some heart failure patients whose heartbeats are uncoordinated have an LVEF less than one-third. In these patients, two-thirds of the blood remains "unpumped" with each heartbeat.

The goal of CRT therapy is to restore coordinated pumping of the ventricles. This is accomplished by a device with separate electrical leads stimulating the two ventricles to contract simultaneously with every heartbeat. CRT devices have improved quality of life and have decreased mortality in some patients with moderate or severe heart failure; an LVEF less than or equal to 35%; and an echocardiogram indicating a slow depolarization of the ventricles (a "QRS" complex greater than 120 ms). Still, about 30% of heart failure patients who receive CRT fail to respond to treatment (see, for example, Jeevanantham et al. (2009) *Cardiol. J.* 16(3)197-209). As one author warned in 2007, "better criteria for identification of the optimal CRT candidate are urgently warranted" (Stellbrink (2007) *Eur. Heart J.* 28:1541-1542). Further, even among heart failure patients who receive CRT intervention, the rate of adverse events such as unplanned hospitalizations for heart failure and death is high (see, for example, Cleland et al. (2005) "The effect of cardiac resynchronization on morbidity and mortality in heart failure." *N. Engl. J. Med.* 352(15):1539-49.

SUMMARY OF THE INVENTION

It has now been discovered that concentrations of the human protein galectin-3 in body fluids can be used to predict or monitor disease progression or therapeutic efficacy in patients treated with cardiac resynchronization therapy. A patient's galectin-3 blood concentration can be monitored after a CRT device is implanted to provide an ongoing indication of disease development or progression and/or of the continued propriety of the course of treatment. For example, the invention permits measurements of changes over time in galectin-3 concentration in a body fluid (e.g., blood, serum, or plasma) of a heart failure patient and comparing the measured change in galectin-3 concentration to changes in galectin-3 concentration observed in other patients for whom cardiac resynchronization therapy was or was not beneficial.

Monitoring methods can include comparing a galectin-3 concentration in a patient to an earlier galectin-3 concentration in the same patient before or after implantation of a CRT device. The methods can also include comparing galectin-3 levels measured at several times following implantation of the CRT device to develop a history of galectin-3 concentrations. For example, the invention provides methods for assessing a patient by detecting the presence or absence of an increasing or decreasing galectin-3 concentration in a body fluid (e.g., blood, serum, or plasma) of a heart failure patient in whom a CRT device has been implanted. The presence of an increasing galectin-3 concentration over time is indicative of a worsening congestive heart failure in the patient.

In one embodiment, the invention provides methods for predicting the prognosis or outcome for a human treated with cardiac resynchronization therapy. The concentration of galectin-3 in a body fluid, e.g., blood, can be determined for the presence or absence of a galectin-3 concentration indicative of prognosis following cardiac resynchronization therapy. For example, a galectin-3 blood concentration in a human can be measured and compared to a minimum threshold. A galectin-3 blood concentration above the minimum threshold may be indicative of an increased risk of death or hospitalization of the human.

The results of the assessment can be used to inform decisions involving treatment of the patient. For example, if the heart failure patient appears to be therapeutically unresponsive to cardiac resynchronization therapy, based on the patient's galectin-3 concentration or a change in the patient's galectin-3 concentration, other forms of treatment may be preferred, such as angioplasty or other surgery and/or administration of a diuretic, an inotrope, a beta-blocker, a natriuretic peptide, a statin, or a vasodilator.

It has also been discovered that concentrations of the human protein galectin-3 in body fluids can be informative in determining whether a presenting patient may benefit from cardiac resynchronization therapy. In this manner, CRT devices, with or without a defibrillator function, can be implanted in those heart failure patients who are more likely to benefit from the treatment. Thus, it is envisioned that patients who have experienced heart failure or who have been identified as at risk for heart failure will be tested to measure their circulating galectin-3 levels. The measured galectin-3 levels will permit the identification of two groups of patients: those who may benefit from cardiac resynchronization therapy, based on their galectin-3 concentration; and those who are unlikely (or less likely) to benefit. CRT devices would be implanted in those in the first group, whereas other courses of therapy would be selected for those in the second group.

The present invention therefore provides methods for selecting a therapy for a human, who may be suffering from or at risk of heart failure. The methods include measuring a galectin-3 concentration in a sample, such as a blood sample, a serum sample, or a plasma sample. The measured galectin-3 concentration is indicative of whether the patient is likely to respond favorably to cardiac resynchronization therapy. Favorable responses include, for example, an increased likelihood of survival over a period of time, or a reduced progression or development of heart failure, improved heart strength, increased LVEF, fewer unplanned hospitalizations for worsening heart failure, increase in peak oxygen consumption during exercise, decreased fatigue, reduced shortness of breath, or reduced sleep apnea.

In one embodiment, the method includes measuring a galectin-3 concentration in a body fluid (e.g., blood, serum, or plasma) of a heart failure patient who is a candidate for cardiac resynchronization therapy, prior to such treatment, and comparing the galectin-3 concentration to a galectin-3 concentration observed in other patients treated with CRT devices, with or without defibrillator functions, for whom cardiac resynchronization therapy has proven beneficial.

Similarly, the invention provides a method for assessing a candidate (e.g., a heart failure patient) for cardiac resynchronization therapy. The method includes measuring a galectin-3 concentration in a body fluid of a patient who is a candidate for cardiac resynchronization therapy and comparing the measured galectin-3 concentration to a reference galectin-3 concentration. The reference galectin-3 concentration can be derived from observed concentrations of galectin-3 in other patients, and can be indicative of responsiveness or non-responsiveness to implantation of a CRT device. Cardiac resynchronization therapy can be restricted or refused if the measured galectin-3 concentration is different than a reference galectin-3 concentration.

The invention also provides methods for treating a human, who may be suffering from or at risk of heart failure; the methods include implanting a CRT device, with or without pacemaker or defibrillator functions, in a patient having a determined galectin-3 blood concentration that is indicative of a favorable response to cardiac resynchronization therapy. In contrast to the methods of selecting a therapy, which involve the process of measuring a galectin-3 blood concentration, the treatment methods relate to the subsequent implantation of the CRT device. Thus, the treatment methods involve the implantation of a CRT device in a patient whose galectin-3 blood concentration has been determined to be indicative of a favorable response, regardless of how the galectin-3 determination was previously made, or by whom.

In a selected or treated patient, the blood concentration of galectin-3 may be determined to be above a minimum threshold, below a maximum threshold or within a target range defined by a minimum and a maximum threshold. The minimum threshold may be, for example, more than 10 ng/ml; between 10 and 15 ng/ml; between 15 and 20 ng/ml; between 20 and 25 ng/ml; between 25 and 30 ng/ml; or be more than 30 ng/ml. The maximum threshold may be, for example, below 70 ng/ml; below 60 ng/ml; below 40 ng/ml; between 30 and 40 ng/ml; between 25 and 30 ng/ml; between 20 and 25 ng/ml; or between 15 and 20 ng/ml.

The results of the assessment can be used to inform decisions involving treatment of the patient. For example, if a heart failure patient's galectin-3 concentration is dissimilar to those of other heart failure patients for whom cardiac resynchronization therapy has proven beneficial, implantation of a CRT device may not be indicated, and the patient may be offered a different medication or therapeutic option.

DETAILED DESCRIPTION OF THE INVENTION

Applicants have invented a method of predicting and/or monitoring a heart failure patient's physiological response to cardiac resynchronization therapy. In past clinical studies, between one quarter and one half of CRT device recipients were classified as "non-responders" because they failed to show significant benefit from the device (Hawkins et al. (2006) Eur. Heart J. 27:1270-1281). One study reported heart failure worsened in 40% of CRT device recipients after implantation, although a control group fared even more poorly (Cleland et al. (2005) New Engl. J. Med. 352:1539-49). Applicants have discovered that measuring the circulating galectin-3 levels in a patient can be used to identify those patients who are better candidates for cardiac resynchronization therapy. In this way, the therapy can be directed preferentially to those more likely to benefit from it, while other patients can be spared the risk and expense and directed to different courses of therapy. In addition, applicants have discovered that measuring galectin-3 upon and/or after a CRT device is implanted provides an ongoing indication of disease development or progression and/or of the continued propriety of the course of treatment.

The terms "heart failure," "HF," "congestive heart failure," or "CHF" as used herein, refer to the complex clinical syndrome that impairs the ability of the ventricle to fill with or eject blood. Any structural or functional cardiac disorder can cause HF, with the majority of HF patients having impaired left ventricular (LV) myocardial function. Symptoms of HF include dyspnea (shortness of breath), fatigue, and fluid retention. The American Heart Association (AHA) has identified 4 stages in the progression or development of HF. Patients in stages A and B show clear risk factors but have not yet developed HF. Patients in stages C and D currently exhibit or in the past have exhibited symptoms of HF. For example, Stage A patients are those with risk factors such as coronary artery disease, hypertension or diabetes mellitus who do not show impaired left ventricular (LV) function. Stage B patients are asymptomatic, but have cardiac structural abnormalities or remodeling, such as impaired LV function, hypertrophy or geometric chamber distortion. Stage C patients have cardiac abnormalities and are symptomatic. Stage D patients have refractory HF in which they exhibit symptoms despite maximal medical treatment. They are typically recurrently hospitalized or unable to leave the hospital without specialized intervention.

Galectin-3 is a structurally unique member of a family of multifunctional β-galactoside-binding lectins (Gabius (2006) Crit. Rev. Immunol. 26:43-79). Expression of galectin-3 has been associated with the epithelium and inflammatory cells including macrophages, neutrophils and mast cells. Galectin-3 has been implicated in a variety of biological processes important in heart failure including myofibroblast proliferation, fibrogenesis, tissue repair, cardiac remodeling, and inflammation (Liu et al. (2009) Am. J. Physiol. Heart Circ. Physiol. 296(2):H404-12; Papaspyridonos et al. (2008) Arterioscler. Thromb. Vasc. Biol. 28(3):433-40; Henderson et al. (2006) Proc. Natl. Acad. Sci. USA 103:5060-5065; Sharma et al. (2004) Circulation 110:3121-3128; Sano et al. (2000) J. Immunol. 165(4):2156-64; Kuwabara et al. (1996) J. Immunol. 156(10):3939-44).

Applicants have developed methods permitting the use of circulating galectin-3 protein levels to predict efficacy of cardiac resynchronization therapy in heart failure patients. Knowledge of a patient's galectin-3 level is informative of patient outcome upon implantation of a CRT device. Furthermore, levels of circulating biomarkers such as galectin-3 levels after implantation are informative of patient outcome, and changes in galectin-3 levels may indicate a changing prognosis. Although higher concentrations of galectin-3 correlate with poor prognosis, such as death and hospitalization, patients with relatively high galectin-3 levels who receive CRT devices may benefit significantly, as measured by heart output, quality of life (as measured, for example, by the Minnesota Living With Heart Failure® Questionnaire, University of Minnesota), reduced progression or development of heart failure, decreased fatigue, reduced shortness of breath, or enhanced likelihood of survival.

Galectin-3 Detection

The present invention provides methods for predicting and/or monitoring the physiological response of a heart failure patient to cardiac resynchronization therapy by measuring the levels of markers such as galectin-3, optionally in combination with one or more other markers (e.g., BNP, NT-proBNP). Many methods for detecting of a protein of interest, with or without quantitation, are well known and can be used in the practice of the present invention. Examples of such assays are described below and can include, for example, immunoassays, chromatographic methods, and mass spectroscopy. Such assays can be performed on any biological sample including, among others, blood, plasma, and serum. Accordingly, multiple assays can be used to detect galectin-3, and samples can be analyzed from one or more sources.

Markers can be detected or quantified in a sample with the help of one or more separation methods. For example, suitable separation methods may include a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, or atmospheric pressure photoionization mass spectrometry (APPI-MS), APPI-MS/MS, and APPI-(MS)$^n$. Other mass spectrometry methods may include, inter alia, quadrupole, fourier transform mass spectrometry (FTMS) and ion trap. Spectrometric techniques that can also be used include resonance spectroscopy and optical spectroscopy.

Other suitable separation methods include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE), or other chromatographic techniques, such as thin-layer, gas or liquid chromatography, or any combination thereof. In one embodiment, the biological sample to be assayed may be fractionated prior to application of the separation method.

Markers can may be detected or quantified by methods that do not require physical separation of the markers themselves. For example, nuclear magnetic resonance (NMR) spectroscopy may be used to resolve a profile of a marker from a complex mixture of molecules. An analogous use of NMR to classify tumors is disclosed in Hagberg (1998) *NMR Biomed.* 11:148-56, for example.

A marker in a sample also may be detected or quantified, for example, by combining the marker with a binding moiety capable of specifically binding the marker. The binding moiety may include, for example, a member of a ligand-receptor pair, i.e., a pair of molecules capable of having a specific binding interaction. The binding moiety may also include, for example, a member of a specific binding pair, such as antibody-antigen, enzyme-substrate, nucleic acid-nucleic acid, protein-nucleic acid, protein-protein, or other specific binding pairs known in the art. Binding proteins may be designed which have enhanced affinity for a target. Optionally, the binding moiety may be linked with a detectable label, such as an enzymatic, fluorescent, radioactive, phosphorescent or colored particle label. The labeled complex may be detected, e.g., visually or with the aid of a spectrophotometer or other detector, or may be quantified.

Galectin-3 levels can be quantitated by performing an immunoassay. A galectin-3 immunoassay involves contacting a sample from a subject to be tested with an appropriate antibody under conditions such that immunospecific binding can occur if galectin-3 is present, and detecting or measuring the amount of any immunospecific binding by the antibody. Any suitable immunoassay can be used, including, without limitation, competitive and non-competitive assay systems using techniques such as Western blots, radioimmunoassays, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays and protein A immunoassays.

In a "sandwich" assay, two molecules ("binding moieties") such as monoclonal antibodies that specifically bind to non-overlapping sites (epitopes) on galectin-3 are used. Typically, one binding moiety is immobilized on a solid surface where it binds with and captures galectin-3. This first binding moiety is therefore also referred to as the capture binding moiety. A second binding moiety is detectably labeled, for example, with a fluorophore, enzyme, or colored particle, such that binding of the second binding moiety to the galectin-3-complex indicates that galectin-3 has been captured. The intensity of the signal is proportional to the concentration of galectin-3 in the sample. The second binding moiety is therefore also referred to as the detection binding moiety or label binding moiety. A binding moiety can be any type of molecule, as long as it specifically binds to a portion of the N-terminus of galectin-3. In a preferred embodiment, the binding moieties used are monoclonal anti-galectin-3 antibodies, i.e., monoclonals raised against or otherwise selected to bind to separate portions of galectin-3.

Such assay procedures can be referred to as two-site immunometric assay methods, "sandwich" methods or (when antibodies are the binders) "sandwich immunoassays." As is known in the art, the capture and detection antibodies can be contacted with the test sample simultaneously or sequentially. Sequential methods can be accomplished by incubating the capture antibody with the sample, and adding the labeled detection antibody at a predetermined time thereafter (sometimes referred to as the "forward" method). Alternatively, the labeled detection antibody can be incubated with the sample first and then the sample can be exposed to the capture antibody (sometimes referred to as the "reverse" method). After any necessary incubation(s), which may be of short duration, to complete the assay, the label is measured. Such assays may be implemented in many specific formats known to those of skill in the art, including through use of various high throughput clinical laboratory analyzers or with a point of care or home testing device.

In one embodiment, a lateral flow device may be used in the sandwich format wherein the presence of galectin-3 above a baseline sensitivity level in a biological sample will permit formation of a sandwich interaction upstream of or at the capture zone in the lateral flow assay. See, for example, U.S. Pat. No. 6,485,982. The capture zone may contain capture binding moieties such as antibody molecules, suitable for capturing galectin-3, or immobilized avidin or the like for capture of a biotinylated complex. See, for example, U.S. Pat. No. 6,319,676. The device may also incorporate a luminescent label suitable for capture in the capture zone, the concentration of galectin-3 being proportional to the intensity of the signal at the capture site. Suitable labels include fluorescent labels immobilized on polystyrene microspheres. Colored particles also may be used.

Other assay formats that may be used in the methods of the invention include, but are not limited to, flow-through devices. See, for example, U.S. Pat. No. 4,632,901. In a flow-through assay, one binding moiety (for example, an antibody) is immobilized to a defined area on a membrane surface. This membrane is then overlaid on an absorbent layer that acts as a reservoir to pump sample volume through the device. Following immobilization, the remaining protein-binding sites on the membrane are blocked to minimize non-specific interactions. In operation, a biological sample is added to the membrane and filters through the matrix, allowing any analyte specific to the antibody in the sample to bind to the immobilized antibody. In a second step, a labeled secondary antibody may be added or released that reacts with captured marker to complete the sandwich. Alternatively, the secondary antibody can be mixed with the sample and added in a single step. If galectin-3 is present, a colored spot develops on the surface of the membrane.

The most common enzyme immunoassay is the "Enzyme-Linked Immunosorbent Assay (ELISA)." ELISA is a technique for detecting and measuring the concentration of an antigen using a labeled (e.g., enzyme-linked) form of the antibody. There are different forms of ELISA, which are well known to those skilled in the art. Standard ELISA techniques are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984), *J. Clin. Chem. Clin. Biochem.* 22:895-904. A preferred enzyme-linked immunosorbent assay kit (ELISA) for detecting galectin-3 is commercially available (BG Medicine, Waltham, Mass.).

In a "sandwich ELISA," an antibody (e.g., anti-galectin-3) is linked to a solid phase (i.e., a microtiter plate) and exposed to a biological sample containing antigen (e.g., galectin-3). The solid phase is then washed to remove unbound antigen. A labeled antibody (e.g., enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and β-galactosidase. The enzyme linked antibody reacts with a substrate to generate a colored reaction product that can be measured. Any of the immunoassays described herein suitable for use with the kits and methods of the present invention can also use any binding moiety in the place of an antibody.

A detailed review of immunological assay design, theory and protocols can be found in numerous texts in the art, including Butt, W. R., *Practical Immunology*, ed. Marcel Dekker, New York (1984) and Harlow et al. *Antibodies, A Laboratory Approach*, ed. Cold Spring Harbor Laboratory (1988).

In general, immunoassay design considerations include preparation of antibodies (e.g., monoclonal or polyclonal antibodies) having sufficiently high binding specificity for the target to form a complex that can be distinguished reliably from products of nonspecific interactions. As used herein, the term "antibody" is understood to mean binding proteins, for example, antibodies or other proteins comprising an immunoglobulin variable region-like binding domain, having the appropriate binding affinities and specificities for the target. The higher the antibody binding specificity, the lower the target concentration that can be detected. As used herein, the terms "specific binding" or "binding specifically" are understood to mean that the binding moiety, for example, a binding protein, has a binding affinity for the target of greater than about $10^5$ $M^{-1}$, more preferably greater than about $10^7$ $M^{-1}$.

Antibodies to an isolated target marker which are useful in assays for detecting heart failure in an individual may be generated using standard immunological procedures well known and described in the art. See, for example *Practical Immunology*, supra. Briefly, an isolated marker is used to raise antibodies in a xenogeneic host, such as a mouse, goat or other suitable mammal. The marker is combined with a suitable adjuvant capable of enhancing antibody production in the host, and is injected into the host, for example, by intraperitoneal administration. Any adjuvant suitable for stimulating the host's immune response may be used. A commonly used adjuvant is Freund's complete adjuvant (an emulsion comprising killed and dried microbial cells and available from, for example, Calbiochem Corp., San Diego, or Gibco, Grand Island, N.Y.). Where multiple antigen injections are desired, the subsequent injections may comprise the antigen in combination with an incomplete adjuvant (e.g., cell-free emulsion). Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target and have the desired binding affinity.

Exemplary epitopes from the N-terminus of galectin-3 include, but are not limited to, MADNFSLHDALS (SEQ ID NO:1); MADNFSLHDALSGS (SEQ ID NO:2); WGNQPAGAGG (SEQ ID NO:3); YPGAPGAYPGAPAPGV (SEQ ID NO:4); GNPNPQGWPGA (SEQ ID NO:5); YPSSGQPSATGA (SEQ ID NO:6); YPGQAPPGAYPGQAPPGA (SEQ ID NO:7); YPGAPAPGVYPGPPSGPGA (SEQ ID NO:8); and YPSSGQPSATGA (SEQ ID NO:9). Other galectin-3 epitopes, including non-linear epitopes, can also be used as targets for detection by an anti-galectin-3 antibody. Exemplary antibodies are discussed in U.S. 2010/014954, the entire contents of which are incorporated herein by reference.

Antibody binding domains also may be produced biosynthetically and the amino acid sequence of the binding domain manipulated to enhance binding affinity with a preferred epitope on the target. Specific antibody methodologies are well understood and described in the literature. A more detailed description of their preparation can be found, for example, in *Practical Immunology*, (supra).

In addition, genetically engineered biosynthetic antibody binding sites, also known in the art as BABS or sFv's, may be used to determine if a sample contains a marker. Methods for making and using BABS comprising (i) non-covalently associated or disulfide bonded synthetic $V_H$ and $V_L$ dimers, (ii) covalently linked $V_H$-$V_L$ single chain binding sites, (iii) individual $V_H$ or $V_L$ domains, or (iv) single chain antibody binding sites are disclosed, for example, in U.S. Pat. Nos. 5,091,513; 5,132,405; 4,704,692; and 4,946,778. Furthermore, BABS having requisite specificity for the marker can be derived by phage antibody cloning from combinatorial gene libraries (see, for example, Clackson et al. *Nature* 352: 624-628 (1991)). Briefly, phages, each expressing on their coat surfaces BABS having immunoglobulin variable regions encoded by variable region gene sequences derived from mice pre-immunized with an isolated marker, or a fragment thereof, are screened for binding activity against the immobilized marker. Phages which bind to the immobilized marker are harvested and the gene encoding the BABS is sequenced. The resulting nucleic acid sequences encoding the BABS of interest then may be expressed in conventional expression systems to produce the BABS protein.

Multimarker analysis can be used to improve the accuracy of diagnosis and monitoring. For example, blood concentrations of galectin-3 (Gal-3) and brain natriuretic peptide (BNP) can be used to diagnose heart failure and to predict the long-term outcome of heart failure (van Kimmenade et al., *J. Am. Coll. Cardiol.*, 48:1217-24 (2006); Sharma et al., *Circulation*, 110:3121-28 (2004); Lok et al., *Eur. Heart J.*, 28:141, Abstract 1035 (2007)). BNP and its cleavage equivalent amino-terminal proBNP (NT-proBNP) are elevated in heart muscle and in blood during heart failure as a result of high filling pressures of heart chambers and the stretch of cardiac muscle fibers. Other secondary markers that could be used to diagnose heart failure may include non-polypeptidic cardiac markers such as sphingolipid, sphingosine, sphingosine-1-phosphate, dihydrosphingosine and sphingosylphosphorylcholine (see U.S. Pat. No. 6,534,322). When measuring the levels of the above markers, corrections for age and gender may be incorporated to improve the accuracy of diagnosis.

Treatment Methods

Patients whose galectin-3 levels identify them as candidates for cardiac resynchronization therapy can be treated by implantation of a CRT device.

Traditional pacemakers include one or two electrical leads placed in the right atrium, the right ventricle, or both, to pace their contractions. CRT devices include at least two leads: one in the right ventricle, and one in the coronary sinus against the wall of the left ventricle, to induce simultaneous contractions of the left and right ventricles. Often, a third, sensing lead is placed in the right atrium to provide data to time the ventricular contractions. Such CRT devices not only promote the coordinated contraction of the left and right ventricles, but also ensure their timing with respect to the contraction of the atria. The leads are connected to a battery-powered pulse generator implanted in the chest, beneath the skin. After the atrial contractions fill the ventricles with blood, the pulse generator sends small electrical signals to the ventricles, stimulating their coordinated contraction, expelling the blood from the heart and pumping it through the circulatory system.

CRT devices are available with or without an associated defibrillator function. Devices that include a defibrillator function are sometimes referred to as CRT-D devices. CRT-D devices are particularly useful in patients at risk of abnormal heart rhythms. For example, a rapid, irregular heartbeat can prevent the heart from completing a full contraction; very slow heartbeats can also be dangerous. If the heart develops an abnormal rhythm, a CRT-D device can shock the heart, disrupting the abnormal rhythm and giving the heart the opportunity to resume a more normal speed.

CRT devices are widely available from manufacturers such as St. Jude Medical (Atlas® II HF ICD, Atlas®+ HF ICD, Epic® HF ICD, Epic® II HF ICD, Promote® RF CRT-D), Boston Scientific (COGNIS®, Contak Renewal, LIVIAN™), Medtronic (Consulta™, Concerto®, Maximo® II, InSync® Maximo®), Sorin Group ERM (OVATIO™ and NewLiving™), and BIOTRONIK® (Stratos® LV and Stratos® LV-T).

Cardiac resynchronization therapy is optionally combined with one or more other treatments for heart failure. For example, a patient may also be treated with: a statin, such as rosuvastatin, atorvastatin, pravastatin, fluvastatin, lovastatin, pitavastatin, or simvastatin; a diuretic, such as furosemide, bumetanide, hydrochlorothiazide, spironolactone, eplerenone, triamterene, torsemide, or metolazone; an inotrope, such as dobutamine, milrinone, or digoxin; a beta-blocker, such as carvediol or metoprolol; and/or a natriuretic peptide, such as BNP.

Treatments can also include a vasodilator, such as: an angiotensin-converting enzyme (ACE) inhibitor (e.g. captopril, enalapril, lisinopril, benazepril, quinapril, fosinopril, or ramipril); an angiotensin II receptor blocker, such as candesartan, irbesartan, olmesartan, losartan, valsartan, telmisartan, or eprosartan; a nitrate, such as isosorbide mononitrate or isosorbide dinitrate; and/or hydralazine. Other forms of medical intervention such as angioplasty or other surgery can also be performed in appropriate cases.

The efficacy of therapy can be monitored over time by regular measurement of relevant biomarkers such as galectin-3. Galectin-3 levels and/or other biomarkers (such as BNP) can be measured in a CRT patient and can be compared to a previous galectin-3 concentration measured in the patient. An increase or decrease in galectin-3 concentration relative to one or more previous galectin-3 concentrations in the patient may be an indication that the patient is responding or not responding to cardiac resynchronization therapy. Marker levels can be monitored over time, such as in samples obtained from a patient at annual, semi-annual, bimonthly, monthly, triweekly, biweekly, weekly, daily, or at variable intervals.

EXAMPLE

Galectin-3 and Cardiac Resynchronization Therapy

Methods

Study Population

A clinical trial enrolled patients with heart failure (HF) for at least 6 weeks (New York Heart Association functional class III or IV), with evidence of left ventricular systolic dysfunction and cardiac dyssynchrony (as indicated by QRS width greater than or equal to 150 ms or echocardiographic dyssynchrony if QRS was 120-149 msec). The design and primary results of the trial are reported in published literature [J. Cleland et al., "The effect of cardiac resynchronization on morbidity and mortality in heart failure." *N Engl J. Med.* 2005 Apr. 14; 352(15):1539-49]. All patients received standard pharmacologic therapy including angiotensin converting enzyme inhibitors, beta blockers and diuretics. Patients were randomly assigned to treatment with optimized pharmacological therapy alone or combined with cardiac resynchronization therapy (CRT) in an open-label manner. Patients receiving CRT received an InSync® III CRT device (Medtronic Inc., Minneapolis, Minn.), in addition to their background pharmacological therapy. Atriobiventricular pacing was used, with atrial pacing to prevent rates slower than 60 beats per minute. Right ventricle and left ventricle were stimulated simultaneously. Echocardiography was used to optimize atrio-ventricular delay using the mitral inflow signal. The shortest atrio-ventricular delay that did not shorten the atrial component of the inflow signal was considered optimal.

Blood Sampling

Serum samples were drawn at baseline, at 3 and at 18 months. All samples were stored at −80° C.

Laboratory Analysis

Determination of galectin-3 concentration in serum samples was assessed using ELISA kits (Galectin-3 assay; BG Medicine Inc., Waltham, Mass., USA). The assay sensitivity (lowest concentration different from zero) was 0.96 ng/mL. Intra- and inter-assay variations were less than 8% and 10% respectively.

Statistical Analyses

All analyses were performed using SAS version 9 software (SAS Institute, Cary, N.C., USA). Logistic regression was used to assess the association of analyte levels and outcomes. Only patients complete on all covariates of interest in a particular analysis were considered for inclusion in that analysis. The two-tailed significance level was set to 0.05, and probability values less than 0.05 were considered significant.

Results

Galectin-3 Concentration Over Time in Patients

The mean and standard deviation of galectin-3 at baseline, which is defined as the time of enrollment in the study, and at 18 months after baseline are shown in Table 1 below, by intervention group. Note that not all patients had a serum sample available for galectin-3 measurement at each time point; Table 1 presents results for all patients with a galectin-3 measurement available.

TABLE 1

Serum galectin-3 concentrations (mean and standard deviation) at baseline and at 18 months after baseline, by intervention group.

|  | Patients who received CRT | Patients who did not receive CRT |
|---|---|---|
| Baseline | 28.0 (14.8) ng/mL [N = 124] | 26.8 (8.8) ng/mL [N = 122] |
| Month 18 | 26.4 (10.6) ng/mL [N = 84] | 26.8 (10.5) ng/mL [N = 75] |

Numbers in parentheses indicate one standard deviation. The number of patients who had serum samples with galectin-3 measurement is also indicated in the Table for each time point and group.

It is observed from Table 1 that the mean serum galectin-3 concentration in patients who did not receive CRT is identical at baseline and 18 months after baseline, whereas the mean serum galectin-3 concentration in patients who did receive CRT decreased between baseline and 18 months.

Galectin-3 Concentration Over Time in Patients, and Adverse Outcome

The frequency of an adverse outcome, namely death or unplanned hospitalization for heart failure within 18 months after baseline, was investigated for the 10 patients who experienced the greatest reduction of serum galectin-3 between baseline and 3 months after baseline. It was observed that out of the 10 patients with the greatest reduction in galectin-3 levels between baseline and 3 months after baseline, 6 of these patients (60%) suffered the adverse outcome of death or hospitalization for heart failure within 18 months of baseline. In contrast, of the other patients with a serum galectin-3 value at baseline and at 3 months after baseline and available information on adverse outcome, 81% (128 patients out of 159 patients) suffered the adverse outcome of death or hospitalization for heart failure at 18 months.

Galectin-3 Concentration at Baseline in Patients Receiving CRT are Associated with Adverse Outcome It was observed that baseline galectin-3 serum concentration was significantly associated with the risk of a subsequent adverse outcome, namely death within 18 months or hospitalization within 18 months, in patients who received CRT. Table 2 below displays the results of a statistical logistic regression analysis to assess the association between baseline galectin-3 and subsequent adverse outcome. For details on the technique of logistic regression, see e.g. David W. Hosmer and Stanley Lemeshow, *Applied logistic regression* (New York: Wiley, 2000). In the analysis, data from patients with a baseline galectin-3 levels greater than 30 ng/mL were placed into one group, and data from patients with baseline galectin-3 levels less than or equal to 30 ng/mL were placed into a separate group. In addition, the left ventricular end systolic volume (LVESV) for each patient was also considered in the statistical model as a covariate; as such, only the 98 patients who had measurements of both variables at baseline are able to be included in this analysis. Patients who received a CRT and who had a baseline galectin-3 level above 30 ng/mL had an approximately three times higher odds of death within 18 months or hospitalization within 18 months compared to patients who received a CRT and who had a baseline galectin-3 level less than or equal to 30 ng/mL.

TABLE 2

Results of logistic regression analysis for the endpoint of death or hospitalization within 18 months, for patients who received CRT.

| Variable | Odds Ratio and 95% confidence interval (95% CI) | P-value |
|---|---|---|
| Baseline Galectin-3 > 30 ng/mL | 3.31 (95% CI: 1.17-9.32) | 0.024 |
| Baseline LVESV > 200 mL | 2.81 (95% CI: 0.99-7.93) | 0.051 |

Odds ratio for galectin-3 is relative to the group with baseline galectin-3 less than or equal to 30 ng/mL; odds ratio for LVESV is relative to the group with LVESV less than or equal to 200 mL.

Galectin-3 Concentrations at Baseline are Significantly Associated with Outcome Among Patients Who Received CRT but not Among Patients Who Did not Receive CRT It was observed that baseline galectin-3 serum concentration was significantly associated with the risk of a subsequent adverse outcome, namely death within 18 months or unplanned hospitalization within 18 months of baseline, in patients who received CRT, but not in patients who did not receive CRT. Table 3 below displays the results of a statistical logistic regression analysis to assess the association between baseline galectin-3 and subsequent adverse outcome. This analysis was performed separately for patients who received CRT, and for patients who did not receive CRT. For details on the technique of logistic regression, see e.g. David W. Hosmer and Stanley Lemeshow, *Applied logistic regression* (New York: Wiley, 2000). In the analyses, data from patients with a baseline galectin-3 levels greater than 30 ng/mL were placed into one group, and data from patients with baseline galectin-3 levels less than or equal to 30 ng/mL were placed into a separate group. In addition, the left ventricular end systolic volume (LVESV) for each patient was also considered in the statistical models as a covariate. Table 3 presents the results of these analyses. There were 98 evaluable patients who received CRT, of whom 22 (22.4% of 98) experienced an adverse outcome of death or hospitalization within 18 months. There were 96 evaluable patients who did not receive CRT, of whom 29 (30.2% of 96) experienced an adverse outcome of death or hospitalization within 18 months.

TABLE 3

Results of logistic regression analysis for the endpoint of death or hospitalization within 18 months, analyzed separately for patients who received CRT and for patients who did not receive CRT.

|  | Patients who received CRT | | Patients who did not receive CRT | |
|---|---|---|---|---|
| Variable | Odds Ratio and 95% confidence interval (95% CI) | P-value | Odds Ratio and 95% confidence interval (95% CI) | P-value |
| Baseline Galectin-3 > 30 ng/mL | 3.31 (95% CI: 1.17-9.32) | 0.024 | 2.92 (95% CI: 0.99-8.54) | 0.051 |
| Baseline LVESV > 200 mL | 2.81 (95% CI: 0.99-7.93) | 0.051 | 3.96 (95% CI: 1.38-11.38) | 0.011 |

Odds ratio for galectin-3 is relative to the group with baseline galectin-3 less than or equal to 30 ng/mL; odds ratio for LVESV is relative to the group with LVESV less than or equal to 200 mL.

It was found that only among patients who received CRT was baseline galectin-3 statistically significantly associated with the adverse outcome of death or hospitalization within 18 months with the pre-specified statistical significance level. Baseline galectin-3 in the group of patients who did not receive CRT was not significantly associated with the same adverse outcome endpoint at the prescribed significance level of less than 0.05, and the 95% confidence interval in that group overlapped the null odds ratio value of 1, or unity.

CRT is Associated with Reduced Event Rates Overall but with a Larger Reduction in Patients with Higher Galectin-3 Concentrations The number of patients in each of four categories who experienced an event of death or unplanned hospitalization for heart failure within 18 months of baseline is enumerated in Table 4 below. This table includes all patients from the study whose baseline blood sample had a galectin-3 baseline concentration value, and who were successfully followed for 18 months such that the endpoint of death or unplanned hospitalization for heart failure within 18 months of baseline could be ascertained.

TABLE 4

Numbers of patients, by CRT treatment and galectin-3 category. The number and percentage of events is indicated in each cell of the table. The event in this table is defined as death or unplanned hospitalization for heart failure within 18 months of baseline.

|  | Patients who received CRT | Patients who did not receive CRT |
|---|---|---|
| Baseline Galectin-3 > 30 ng/mL | Events: 10<br>No events: 20<br>Percentage experiencing event: 10/(10 + 20) = 33.3% | Events: 12<br>No events: 16<br>Percentage experiencing event: 42.9% |
| Baseline Galectin-3 ≤ 30 ng/mL | Events: 15<br>No events: 66<br>Percentage experiencing event: 18.5% | Events: 21<br>No events: 55<br>Percentage experiencing event: 27.6% |

As may be observed from Table 4, patients who received CRT exhibited a decreased event frequency compared to patients who did not receive CRT. It is noted that in the low galectin-3 group, namely patients with baseline galectin-3 levels ≤30 ng/mL, the absolute reduction in event frequency was 9.1% (27.6% minus 18.5%). In the high galectin-3 group, namely patients with baseline galectin-3 levels >30 ng/mL, the absolute reduction in event frequency was 9.6% (42.9% minus 33.3%). These data likely indicate that higher baseline galectin-3 values identify patients who exhibit a larger benefit from CRT, because the 9.6% reduction in the higher baseline galectin-3 group is greater than the 9.1% reduction in the lower baseline galectin-3 group.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of predicting responsiveness to cardiac resynchronization therapy of a human who is a candidate for or has been treated with cardiac resynchronization therapy, the method comprising measuring a galectin-3 blood concentration in a sample from the human, thereby to determine presence or absence of a galectin-3 blood concentration in the human predictive of responsiveness to cardiac resynchronization therapy, wherein the galectin-3 blood concentration in the human is determined to be above a minimum threshold of between 25 and 30 ng/ml, and wherein the measuring is performed using an immunoassay comprising the steps:
   contacting the sample with a first antibody immobilized on a solid surface and capable of binding to galectin-3, wherein the first antibody captures the galectin-3 in the sample to form a first complex;
   contacting the first complex with a second antibody comprising a detectable label and capable of binding to galectin-3, wherein the second antibody binds to the first complex to form a second complex comprising the detectable label; and
   detecting the detectable label of the second complex, thereby detecting the galectin-3 blood concentration in the sample.

2. The method of claim 1, wherein the human is a candidate for cardiac resynchronization therapy.

3. The method of claim 1, wherein the human has been treated with cardiac resynchronization therapy.

4. The method of claim 1, wherein the sample comprises blood, serum or plasma.

5. The method of claim 1, wherein responsiveness comprises improved survival, fewer unplanned hospitalizations for worsening heart failure, improved heart strength, decreased fatigue, reduced shortness of breath, or reduced sleep apnea.

6. The method of claim 1, wherein the galectin-3 blood concentration in the human is determined to be within a target range.

7. A method of predicting responsiveness to cardiac resynchronization therapy of a human who is a candidate for or has been treated with cardiac resynchronization therapy, the method comprising measuring a galectin-3 blood concentration in a sample from the human, thereby to determine presence or absence of a galectin-3 blood concentration in the human predictive of responsiveness to cardiac resynchronization therapy, wherein the galectin-3 blood concentration in the human is determined to be below a maximum threshold of between 25 and 30 ng/ml, and wherein the measuring is performed using an immunoassay comprising the steps:
   contacting the sample with a first antibody immobilized on a solid surface and capable of binding to galectin-3, wherein the first antibody captures the galectin-3 in the sample to form a first complex;
   contacting the first complex with a second antibody comprising a detectable label and capable of binding to galectin-3, wherein the second antibody binds to the first complex to form a second complex comprising the detectable label; and
   detecting the detectable label of the second complex, thereby detecting the galectin-3 blood concentration in the sample.

8. A method of predicting responsiveness to cardiac resynchronization therapy of a human who is a candidate for or has been treated with cardiac resynchronization therapy, the method comprising measuring a galectin-3 blood concentration in a sample from the human, thereby to determine presence or absence of a galectin-3 blood concentration in the human predictive of responsiveness to cardiac resynchronization therapy, wherein the measuring is performed using an immunoassay comprising the steps:
   contacting the sample with a first antibody immobilized on a solid surface and capable of binding to galectin-3, wherein the first antibody captures the galectin-3 in the sample to form a first complex;
   contacting the first complex with a second antibody comprising a detectable label and capable of binding to galectin-3, wherein the second antibody binds to the first complex to form a second complex comprising the detectable label, wherein the first antibody or the second antibody binds to an epitope defined by GNPNPQGWPGA (SEQ ID NO:5); and
   detecting the detectable label of the second complex, thereby detecting the galectin-3 blood concentration in the sample.

9. The method of claim 8, wherein the human is a candidate for cardiac resynchronization therapy.

10. The method of claim 8, wherein the human has been treated with cardiac resynchronization therapy.

11. The method of claim 8, wherein the sample comprises blood, serum or plasma.

12. The method of claim 8, wherein responsiveness comprises improved survival, fewer unplanned hospitalizations for worsening heart failure, improved heart strength, decreased fatigue, reduced shortness of breath, or reduced sleep apnea.

13. The method of claim 8, wherein the galectin-3 blood concentration in the human is determined to be within a target range.

14. The method of claim 8, wherein the galectin-3 blood concentration in the human is determined to be above a minimum threshold.

15. The method of claim 14, wherein the minimum threshold is between 25 and 30 ng/ml.

16. The method of claim 8, wherein the galectin-3 blood concentration in the human is determined to be below a maximum threshold.

17. The method of claim 16, wherein the maximum threshold is between 25 and 30 ng/ml.

18. A method of predicting responsiveness to cardiac resynchronization therapy of a human who is a candidate for or has been treated with cardiac resynchronization therapy, the method comprising measuring a galectin-3 blood concentration in a sample from the human, thereby to determine presence or absence of a galectin-3 blood concentration in the human predictive of responsiveness to cardiac resynchronization therapy, wherein the measuring is performed using an immunoassay comprising the steps:
  contacting the sample with a first antibody immobilized on a solid surface and capable of binding to galectin-3, wherein the first antibody captures the galectin-3 in the sample to form a first complex;
  contacting the first complex with a second antibody comprising a detectable label and capable of binding to galectin-3, wherein the second antibody binds to the first complex to form a second complex comprising the detectable label, wherein the first antibody or the second antibody binds to an epitope defined by YPGQAPPGAYPGQAPPGA (SEQ ID NO:7); and
  detecting the detectable label of the second complex, thereby detecting the galectin-3 blood concentration in the sample.

19. The method of claim 18, wherein the human is a candidate for cardiac resynchronization therapy.

20. The method of claim 18, wherein the human has been treated with cardiac resynchronization therapy.

21. The method of claim 18, wherein the sample comprises blood, serum or plasma.

22. The method of claim 18, wherein responsiveness comprises improved survival, fewer unplanned hospitalizations for worsening heart failure, improved heart strength, decreased fatigue, reduced shortness of breath, or reduced sleep apnea.

23. The method of claim 18, wherein the galectin-3 blood concentration in the human is determined to be within a target range.

24. The method of claim 18, wherein the galectin-3 blood concentration in the human is determined to be above a minimum threshold.

25. The method of claim 24, wherein the minimum threshold is between 25 and 30 ng/ml.

26. The method of claim 18, wherein the galectin-3 blood concentration in the human is determined to be below a maximum threshold.

27. The method of claim 26, wherein the maximum threshold is between 25 and 30 ng/ml.

28. The method of claim 18, wherein detection of galectin-3 further comprises use of an antibody that binds to an epitope defined by GNPNPQGWPGA (SEQ ID NO:5).

29. The method of claim 14, wherein the minimum threshold is more than 10 ng/ml.

30. The method of claim 14, wherein the minimum threshold is between 10 and 15 ng/ml.

31. The method of claim 14, wherein the minimum threshold is between 15 and 20 ng/ml.

32. The method of claim 14, wherein the minimum threshold is between 20 and 25 ng/ml.

33. The method of claim 14, wherein the minimum threshold is more than 30 ng/ml.

34. The method of claim 16, wherein the maximum threshold is below 70 ng/ml.

35. The method of claim 16, wherein the maximum threshold is below 60 ng/ml.

36. The method of claim 16, wherein the maximum threshold is below 40 ng/ml.

37. The method of claim 16, wherein the maximum threshold is between 30 and 40 ng/ml.

38. The method of claim 16, wherein the maximum threshold is between 20 and 25 ng/ml.

39. The method of claim 16, wherein the maximum threshold is between 15 and 20 ng/ml.

40. The method of claim 24, wherein the minimum threshold is more than 10 ng/ml.

41. The method of claim 24, wherein the minimum threshold is between 10 and 15 ng/ml.

42. The method of claim 24, wherein the minimum threshold is between 15 and 20 ng/ml.

43. The method of claim 24, wherein the minimum threshold is between 20 and 25 ng/ml.

44. The method of claim 24, wherein the minimum threshold is more than 30 ng/ml.

45. The method of claim 26, wherein the maximum threshold is below 70 ng/ml.

46. The method of claim 26, wherein the maximum threshold is below 60 ng/ml.

47. The method of claim 26, wherein the maximum threshold is below 40 ng/ml.

48. The method of claim 26, wherein the maximum threshold is between 30 and 40 ng/ml.

49. The method of claim 26, wherein the maximum threshold is between 20 and 25 ng/ml.

50. The method of claim 26, wherein the maximum threshold is between 15 and 20 ng/ml.

51. The method of claim 7, wherein the human is a candidate for cardiac resynchronization therapy.

52. The method of claim 7, wherein the human has been treated with cardiac resynchronization therapy.

53. The method of claim 7, wherein the sample comprises blood, serum or plasma.

54. The method of claim 7, wherein responsiveness comprises improved survival, fewer unplanned hospitalizations for worsening heart failure, improved heart strength, decreased fatigue, reduced shortness of breath, or reduced sleep apnea.

55. The method of claim 7, wherein the galectin-3 blood concentration in the human is determined to be within a target range.

* * * * *

SEQUENCE LISTING

<160> NUMBER OF SEQ ID NOS: 9

<210> SEQ ID NO 1
<211> LENGTH: 12
<212> TYPE: PRT
<213> ORGANISM: Homo sapiens

<400> SEQUENCE: 1

Met Ala Asp Asn Phe Ser Leu His Asp Ala Leu Ser
1               5                   10

<210> SEQ ID NO 2
<211> LENGTH: 14
<212> TYPE: PRT
<213> ORGANISM: Homo sapiens

<400> SEQUENCE: 2

Met Ala Asp Asn Phe Ser Leu His Asp Ala Leu Ser Gly Ser
1               5                   10

<210> SEQ ID NO 3
<211> LENGTH: 10
<212> TYPE: PRT
<213> ORGANISM: Homo sapiens

<400> SEQUENCE: 3

Trp Gly Asn Gln Pro Ala Gly Ala Gly Gly
1               5                   10

<210> SEQ ID NO 4
<211> LENGTH: 16
<212> TYPE: PRT
<213> ORGANISM: Homo sapiens

<400> SEQUENCE: 4

Tyr Pro Gly Ala Pro Gly Ala Tyr Pro Gly Ala Pro Ala Pro Gly Val
1               5                   10                  15

<210> SEQ ID NO 5
<211> LENGTH: 11
<212> TYPE: PRT
<213> ORGANISM: Homo sapiens

<400> SEQUENCE: 5

Gly Asn Pro Asn Pro Gln Gly Trp Pro Gly Ala
1               5                   10

<210> SEQ ID NO 6
<211> LENGTH: 12
<212> TYPE: PRT
<213> ORGANISM: Homo sapiens

<400> SEQUENCE: 6

Tyr Pro Ser Ser Gly Gln Pro Ser Ala Thr Gly Ala
1               5                   10

<210> SEQ ID NO 7
<211> LENGTH: 18
<212> TYPE: PRT
<213> ORGANISM: Homo sapiens

<400> SEQUENCE: 7

Tyr Pro Gly Gln Ala Pro Pro Gly Ala Tyr Pro Gly Gln Ala Pro Pro
1               5                   10                  15

```
Gly Ala

<210> SEQ ID NO 8
<211> LENGTH: 19
<212> TYPE: PRT
<213> ORGANISM: Homo sapiens

<400> SEQUENCE: 8

Tyr Pro Gly Ala Pro Ala Pro Gly Val Tyr Pro Gly Pro Pro Ser Gly
1               5                   10                  15

Pro Gly Ala

<210> SEQ ID NO 9
<211> LENGTH: 12
<212> TYPE: PRT
<213> ORGANISM: Homo sapiens

<400> SEQUENCE: 9

Tyr Pro Ser Ser Gly Gln Pro Ser Ala Thr Gly Ala
1               5                   10
```